United States Patent
Villeger et al.

(10) Patent No.: US 10,456,490 B2
(45) Date of Patent: *Oct. 29, 2019

(54) METHOD OF STERILIZING AN OBJECT WITH ATOMIC NITROGEN FROM A NITROGEN PLASMA

(71) Applicant: SOCIETE POUR LA CONCEPTION DES APPLICATIONS DES TECHNIQUES ELECTRONIQUES, Merignac (FR)

(72) Inventors: Sandrine Villeger, Montjoire (FR); Marie-Agnès Benoit, Merignac (FR)

(73) Assignee: Societe Pour La Conception Des Applications Des Techniques Electroniques, Merignac (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/832,060

(22) Filed: Dec. 5, 2017

(65) Prior Publication Data

US 2019/0142982 A1    May 16, 2019

(30) Foreign Application Priority Data

Nov. 14, 2017 (FR) ...................................... 17 60681

(51) Int. Cl.
*A61L 2/14* (2006.01)
*A61L 2/26* (2006.01)
(Continued)

(52) U.S. Cl.
CPC ................... *A61L 2/14* (2013.01); *A61L 2/24* (2013.01); *A61L 2/26* (2013.01); *H05H 1/00* (2013.01);
(Continued)

(58) Field of Classification Search
CPC ..... A61L 2/14; A61L 2/24; A61L 2/26; A61L 2202/122; A61L 2202/24
See application file for complete search history.

(56) References Cited

U.S. PATENT DOCUMENTS 4,756,882 A * 7/1988 Jacobs ...................... A61L 2/14
422/23
5,186,893 A    2/1993 Moulton et al.
(Continued)

FOREIGN PATENT DOCUMENTS

KR    100920917 B1 * 10/2009
KR    100920917 B1    10/2009

OTHER PUBLICATIONS

Sirajuddin, Plasma Sterilization (Year: 2007).*
(Continued)

*Primary Examiner* — Sean E Conley
*Assistant Examiner* — Brendan A Hensel
(74) *Attorney, Agent, or Firm* — Workman Nydegger

(57) ABSTRACT

A method of sterilizing an object with atomic nitrogen from a nitrogen plasma comprises the steps of positioning the object in a sterilization chamber, and conditioning the object present in the chamber. The step of conditioning includes a first stage of injecting atomic nitrogen into the chamber, during which a first concentration of atomic nitrogen in the chamber is imposed, a suction stage performed after the first injection stage, during which the chamber is evacuated, and a second stage of injecting atomic nitrogen into the chamber that is performed after the suction stage, during which a second concentration of atomic nitrogen is imposed in the chamber. The method further comprises a sterilization step of sterilizing the object, performed after the conditioning, and includes injecting atomic nitrogen into the chamber, during which step a concentration of atomic nitrogen in the chamber is imposed that is greater than the first and second concentrations.

13 Claims, 4 Drawing Sheets

(51) Int. Cl.
*H05H 1/00* (2006.01)
*A61L 2/24* (2006.01)

(52) U.S. Cl.
CPC ..... *A61L 2202/122* (2013.01); *A61L 2202/24* (2013.01)

(56) References Cited

U.S. PATENT DOCUMENTS

| | | | | |
|---|---|---|---|---|
| 5,645,796 | A | * | 7/1997 | Caputo ............... A61L 2/14 422/22 |
| 6,365,102 | B1 | * | 4/2002 | Wu ..................... A61L 2/14 422/23 |
| 2011/0014093 | A1 | | 1/2011 | Ono |
| 2011/0027125 | A1 | * | 2/2011 | Golkowski ......... A61L 2/208 422/29 |

OTHER PUBLICATIONS

Kuen Translation (Year: 2009).*
Bockel et al., "Optical Diagnostics of Active Species in N2 Microwave Flowing Post-Discharges," Surface and Coatings Technology, vol. 74-75, 1995, pp. 474-478.
French Search Report from FR Application No. FR 1760681, dated Jul. 17, 2018.

* cited by examiner

US 10,456,490 B2

METHOD OF STERILIZING AN OBJECT WITH ATOMIC NITROGEN FROM A NITROGEN PLASMA

FIELD OF THE INVENTION

The present invention relates to a method of sterilizing an object by injecting atomic nitrogen from a nitrogen plasma.

BACKGROUND OF THE INVENTION

It is known to sterilize objects by means of an autoclave in which the object that is to be sterilized is raised to a determined high temperature, of about 120° C., with this lasting for determined periods of time and with cycles that are set out by legislation.

Applying a high temperature can raise difficulties and can lead to certain objects being damaged, e.g. when those objects include portions made of polymer material.

Methods that enable sterilization to be performed at lower temperatures have consequently been developed in order to reduce the damage to objects while they are being treated.

In this context, methods of sterilization have been developed by treating the object with a stream of atomic nitrogen from a nitrogen plasma.

Nevertheless, it remains desirable to improve the effectiveness of sterilization by known methods, in particular by reducing the treatment time.

In addition, certain known methods may present a phenomenon of saturation insofar as there may always remain some quantity of microorganisms that are not destroyed by the sterilization treatment, even if the treatment is prolonged. It would be desirable to have a method with improved sterilization effectiveness, without such a saturation phenomenon.

OBJECT AND SUMMARY OF THE INVENTION

In a first aspect, the invention provides a method of sterilizing an object with atomic nitrogen from a nitrogen plasma, the method comprising at least:

positioning the object in a sterilization chamber;

conditioning the object present in the chamber, the conditioning comprising at least:

a first stage of injecting atomic nitrogen into the chamber, during which a first concentration of atomic nitrogen in the chamber is imposed;

a suction stage performed after the first injection stage, during which the chamber is evacuated; and a second stage of injecting atomic nitrogen into the chamber that is performed after the suction stage, during which a second concentration of atomic nitrogen is imposed in the chamber; and a sterilization step of sterilizing the object, performed after the conditioning, comprising injecting atomic nitrogen into the chamber, during which step a concentration of atomic nitrogen in the chamber is imposed that is greater than the first and second concentrations.

The term "atomic nitrogen" should be understood as nitrogen obtained after dissociating of dinitrogen $N_2$ (i.e. the element N).

The atomic nitrogen concentrations imposed in the chamber during conditioning and during the sterilization step may be measured using a spectrophotometer. By way of example, it is possible to use the method described in the publication by Bockel et al.: "Optical diagnostics of active species in $N_2$ microwaves flowing post-discharge" (S. Bockel, A. M. Diamy, and A. Ricard: Surface and coatings technology, 74-75 (1995), 474-478) in order to measure such concentrations of atomic nitrogen. Performing conditioning as described above serves to improve the effectiveness of the sterilization step performed subsequently, while also using a temperature during the method that is limited, lower than 60° C. The inventors consider that the fact of performing the above conditioning in which the sterilizing species (atomic nitrogen) is imposed at a concentration that is lower than the concentration used during the subsequent sterilization step serves to weaken the microorganisms, thereby making the subsequently performed sterilization step more effective.

In an implementation, the conditioning comprises:

a first suction step performed after the first stage of injecting atomic nitrogen, during which the chamber is evacuated;

a stage of injecting molecular nitrogen into the chamber that is performed after the first suction stage; and a second suction stage performed after the stage of injecting molecular nitrogen, during which the chamber is evacuated, the second stage of injecting atomic nitrogen into the chamber being performed after the second suction stage.

The term "molecular nitrogen" should be understood as nitrogen in the dinitrogen state (i.e. the molecule $N_2$).

Performing such an intermediate stage of injecting molecular nitrogen between the first and second injection stages serves to further improve the effectiveness of the sterilization step.

In particular, the duration of the stage of injecting molecular nitrogen may be shorter than at least one of the durations of the first and second stages of injecting atomic nitrogen. In particular, the duration of the stage of injecting molecular nitrogen may be shorter than each of the durations of the first and second stages of injecting atomic nitrogen.

In an implementation, the conditioning further comprises:

a third suction stage performed after the second stage of injecting atomic nitrogen, during which the chamber is evacuated;

a second stage of injecting molecular nitrogen into the chamber, performed after the third suction stage;

a fourth suction stage performed after the second stage of injecting molecular nitrogen, during which the chamber is evacuated; and a third stage of injecting atomic nitrogen into the chamber, performed after the fourth suction stage and during which a third atomic nitrogen concentration is imposed in the chamber;

the atomic nitrogen concentration in the chamber that is imposed during the sterilization step being greater than each of the first, second, and third concentrations.

The fact of performing such a third stage of injecting atomic nitrogen serves to still further improve the effectiveness of the sterilization step.

In an implementation, the conditioning further comprises, after its last stage of injecting atomic nitrogen, a transition stage comprising at least one additional suction stage, during which the chamber is evacuated.

The fact of performing such a transition stage serves to still further improve the effectiveness of the sterilization step.

In particular, the transition stage may comprise two additional suction stages separated by a stage of injecting molecular nitrogen into the chamber.

In an implementation, the pressure reached in the chamber during the injection of atomic nitrogen in the sterilization step is higher than the pressure reached in the chamber during each of the first, second, and optional third stages of injecting atomic nitrogen.

The increase in the concentration of atomic nitrogen during the sterilization step may be obtained by increasing the flow rate with which atomic nitrogen is injected into the chamber and/or by reducing the suction of the content from the chamber. This increase in flow rate or reduction in suction leads to an increase in the pressure in the chamber. Nevertheless, as mentioned below, it is also possible to increase the concentration of atomic nitrogen during the method in other ways.

In particular, the pressure reached in the chamber during the injection of atomic nitrogen in the sterilization step may be greater than or equal to 10 millibars (mbar).

In particular, the pressure reached in the chamber during each of the first, second, and third stages of injecting atomic nitrogen may lie in the range 6 mbar to 10 mbar.

In an implementation, the object is a medical instrument.

BRIEF DESCRIPTION OF THE DRAWINGS

Other characteristics and advantages of the invention appear from the following description given in non-limiting manner with reference to the accompanying drawings, in which.

DETAILED DESCRIPTION OF EMBODIMENTS

Figure 1:
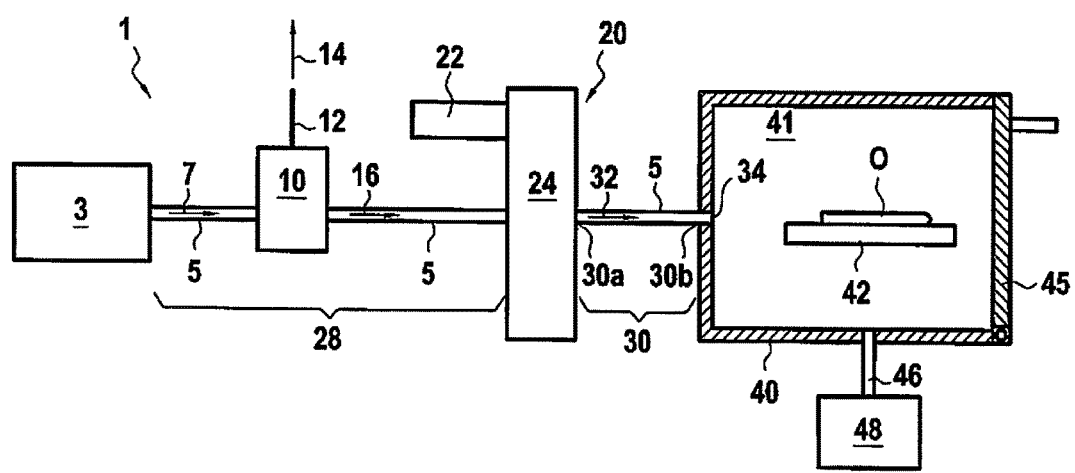
FIG. 1 is a diagram showing an example of a sterilization device suitable for performing a sterilization method of the invention.

FIG. 1 is a diagram of a sterilization device 1 configured to sterilize an object O by treatment with a post-discharge stream of a nitrogen plasma. Such a post-discharge stream comprises a mixture of neutral species, namely atomic nitrogen N and dinitrogen $N_2$.

The device 1 comprises a duct 5 having a first segment 28 putting a compressor 3 into communication with a plasma generator 20. The first segment 28 is provided with a nitrogen filter element 10 situated between the compressor 3 and the plasma generator 20.

A stream 7 of compressed air coming from the compressor 3 flows through the first segment 28 to the filter element 10. The filter element 10 is constituted by an element that is itself known and that is configured to separate dinitrogen from oxygen in the stream 7 of compressed air. After passing through the filter element 10, a stream of dinitrogen 16 flows through the first segment 28 to the plasma generator 20. The oxygen 14 that has been separated from the nitrogen is discharged via an exhaust duct 12.

The first segment 28 enables the stream 16 of dinitrogen to be admitted into the plasma generator 20. The volume content of dinitrogen in the dinitrogen stream 16 admitted into the plasma generator 20 may be greater than or equal to 95%, or indeed greater than or equal to 99%. The dinitrogen stream 16 admitted into the plasma generator 20 may include residual oxygen at a volume content that is less than or equal to 1%. In a variant, the dinitrogen stream 16 admitted into the plasma generator 20 may have no oxygen. In known manner, the plasma generator 20 serves to generate a nitrogen plasma from the nitrogen stream 16. The plasma generator 20 comprises an evacuated enclosure 24 subjected to the action of an electromagnetic field generator that is constituted in this example by a microwave generator 22. The electromagnetic field generated in the enclosure 24 is of sufficiently high intensity to cause the nitrogen to ionize.

The duct has a second segment 30 that puts the plasma generator 20 into communication with a sterilization chamber 40 in which the object O for sterilizing is positioned. The post-discharge stream 32 from the nitrogen plasma flows to the sterilization chamber 40 via the second segment 30.

The sterilization chamber 40 defines a treatment zone 41 including at least one support 42 on which the object O is positioned during the sterilization treatment. The figure shows a treatment zone 41 having a single support 42 and a single object O, however it would naturally not go beyond the ambit of the invention for the treatment zone to have a plurality of supports, each carrying one or more objects. The sterilization chamber 40 is provided with a door 45 to enable the object O to be inserted into the treatment zone 41, and to enable it to be removed after sterilization.

The object O may be a medical instrument such as an endoscope, a chisel, or a scalpel. The invention is also advantageous for sterilizing objects other than medical instruments, such as electronic cards.

The second segment 30 presents a proximal end 30a situated beside the plasma generator 20 and in communication therewith. The second segment 30 also presents a distal end 30b defining an injection orifice 34 for injecting the post-discharge stream 32 into the sterilization chamber 40. The plasma generated by the plasma generator 20 penetrates into the second segment 30 via the proximal end 30a. While the plasma that has been formed is flowing through the second segment 30, ionic and metastable species are destroyed by colliding with one another or with the walls of the duct 5. As a result, an electrically neutral post-discharge stream comprising both atomic nitrogen N and dinitrogen $N_2$ is injected into the chamber 40 via the injection orifice 34. The post-discharge stream 32 flows through the second segment 30 and is injected into the sterilization chamber 40 through the injection orifice 34. The treatment zone 41 is in communication with a vacuum pump 48. This pump draws the post-discharge stream 32 into the treatment zone 41 via a second duct 46 and discharges the gas to the outside.

The example device 1 shown in FIG. 1 has a single injection orifice 34. Naturally, it would not go beyond the ambit of the invention for the post-discharge stream to be injected through a plurality of injection orifices 34.

The example device 1 shown in FIG. 1 serves to inject a post-discharge stream from a nitrogen plasma into the sterilization chamber 40. Under such circumstances, the atomic nitrogen injected during conditioning and during sterilization forms part of a post-discharge stream from a nitrogen plasma. Nevertheless, it would not go beyond the ambit of the invention for the injected atomic nitrogen to be part of a nitrogen plasma.

Two examples of methods of the invention are described with reference to FIGS. 2 and 3. The two examples shown differ by the nature of the sterilization step that is performed after conditioning. In each of these examples, the inventors have observed that performing the conditioning of the invention makes it possible to obtain improved effectiveness of sterilization (see experimental results of FIGS. 4 and 5).

Prior to conditioning C, the method may include a preliminary step EP of reducing pressure, during which the pressure inside the chamber 40 is reduced from atmospheric pressure Pa to a vacuum pressure Pv. This pressure reduction may be performed in non-monotonic manner and may include brief increases of pressure in the chamber 40, as shown. The vacuum pressure Pv reached at the end of this preliminary step EP may be less than or equal to 1 mbar.

Figure 2:
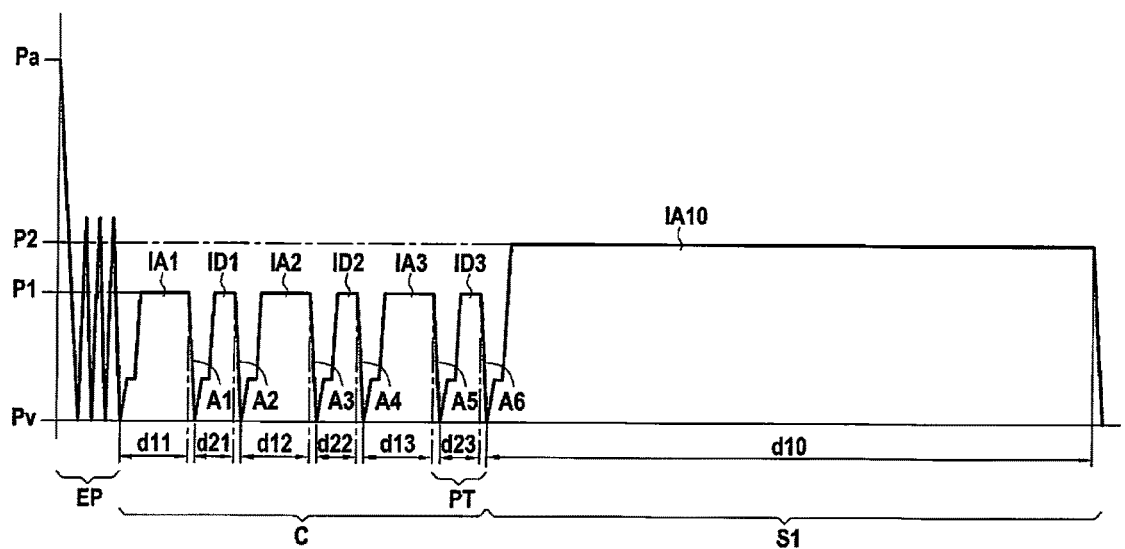
FIG. 2 shows how pressure in the sterilization chamber varies during a first example of a sterilization method of the invention.
Figure 3:
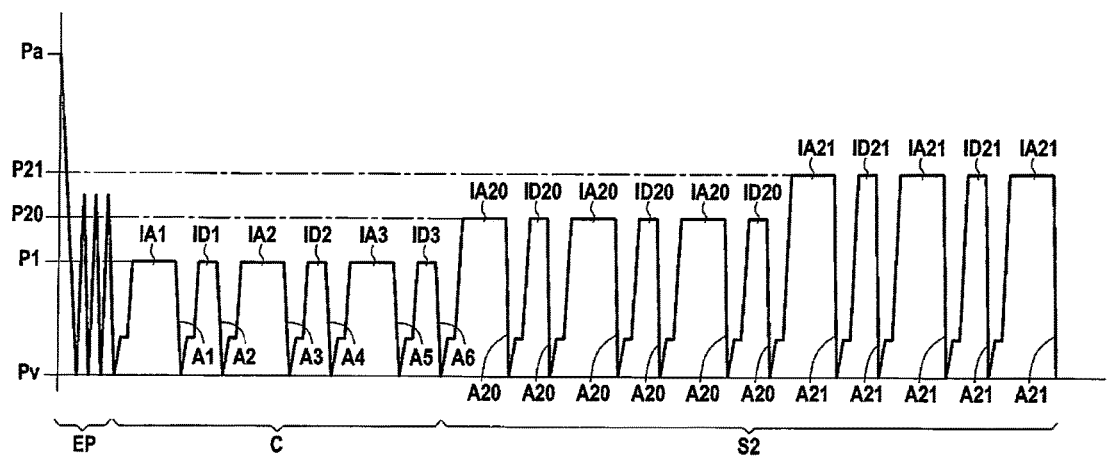
FIG. 3 shows how pressure varies in the sterilization chamber during a second example of a sterilization method of the invention.

The conditioning C performed in the examples of FIGS. 2 and 3 comprises initially a first stage IA1 of injecting atomic nitrogen into the chamber 40, during which a first non-zero concentration of atomic nitrogen is imposed in the chamber 40.

In the example of conditioning C that is shown, the pressure in the chamber 40 increases from the vacuum pressure Pv to a level value P1 during the stage IA1. The pressure in the chamber 40 is then stabilized at this level value P1 during the first injection stage IA1. This level value may lie in the range 6 mbar to 10 mbar. By way of example, the duration $d_{11}$ of the first injection stage IA1 may be greater than or equal to 5 minutes (min), e.g. it may lie in the range 5 min to 15 min.

Thereafter, the injection of atomic nitrogen into the chamber 40 is interrupted.

Thereafter, a first suction stage A1 is performed during which the chamber 40 is evacuated. In this example, the pressure in the chamber 40 decreases progressively from the level value P1 that was reached during the stage IA1, down to the vacuum pressure Pv. The vacuum pressure Pv reached at the end of this first suction stage A1 may be less than or equal to 1 mbar.

The conditioning C is then continued by injecting dinitrogen into the chamber 40 (first stage ID1 of injecting molecular nitrogen). During the stage ID1, the nitrogen is injected in the form of dinitrogen and no longer in atomic form. During the stages of injecting molecular nitrogen, the dinitrogen stream 16 is injected directly into the chamber 40, with the plasma generator 20 being switched off during these stages, unlike stages of injecting atomic nitrogen in which the plasma generator 20 is activated.

In this example, the pressure in the chamber 40 increases from the vacuum pressure Pv to a level value P1 during the stage ID1. The pressure in the chamber 40 is then stabilized at this level value P1 during the first stage ID1 of injecting molecular nitrogen. This level value may lie in the range 6 mbar to 10 mbar. In this example, the level value reached during the stages of injecting molecular nitrogen is shown as being identical to the value reached during the stages of injecting atomic nitrogen (value P1), however it would not go beyond the ambit of the invention if that were not so. The duration $d_{21}$ of the first injection stage ID1 may for example be less than or equal to 5 min, and for example may lie in the range 1 min to 5 min.

Thereafter, the injection of molecular nitrogen into the chamber 40 is interrupted.

A second suction stage A2 is then performed during which the chamber 40 is evacuated. In this example, the pressure in the chamber 40 decreases progressively from the level value P1 reached during the stage ID1 to the vacuum pressure Pv. The vacuum pressure Pv reached at the end of this second suction stage A2 may be less than or equal to 1 mbar.

The conditioning C is then continued by performing a second stage IA2 of injecting atomic nitrogen into the chamber 40 during which a second non-zero concentration of atomic nitrogen is imposed in the chamber 40. The second concentration may be identical to or different from the first concentration.

In the conditioning example C shown, the pressure in the chamber 40 initially increases from the pressure Pv to a level value P1 during the stage IA2. Thereafter, the pressure in the chamber 40 is stabilized at this level value P1, which by way of example may lie in the range 6 mbar to 10 mbar, during the second injection stage IA2. In this example, the level value reached for the pressure are shown to be identical for each of the stages of injecting atomic nitrogen, however it would not go beyond the ambit of the invention if that were not so. The duration $d_{12}$ of the second injection stage IA2 may for example be greater than or equal to 5 min, and for example may lie in the range 5 min to 15 min.

Thereafter, the injection of atomic nitrogen into the chamber 40 is interrupted.

A third suction stage A3 is then performed during which the chamber 40 is evacuated. In this example, the pressure in the chamber 40 decreases progressively from the level value P1 reached during the stage IA2 down to the vacuum pressure Pv. The vacuum pressure Pv reached at the end of this third suction stage A3 may be less than or equal to 1 mbar.

The conditioning C is then continued by performing a second stage ID2 of injecting molecular nitrogen into the chamber 40.

In this example, the pressure in the chamber 40 increases from the vacuum pressure Pv to a level value P1 during the stage ID2. The pressure in the chamber 40 is then stabilized at this level value P1, which for example lies in the range 6 mbar to 10 mbar, during the second stage ID2 of injecting molecular nitrogen. The figure shows that the level value for pressure that is reached during each of the molecular nitrogen injection stages is identical. However, it would not go beyond the ambit of the invention if that were not so. By way of example, the duration $d_{22}$ of the second injection stage ID2 may be less than or equal to 5 min, and for example it may lie in the range 1 min to 5 min.

Thereafter, the injection of molecular nitrogen into the chamber 40 is interrupted.

A fourth suction stage A4 is then performed during which the chamber 40 is evacuated. In this example, the pressure in the chamber 40 decreases progressively from the level value P1 reached during the stage ID2 down to the vacuum pressure Pv. The vacuum pressure Pv reached at the end of this fourth suction stage A4 may for example be less than or equal to 1 mbar.

The conditioning C is then continued by performing a third stage IA3 of injecting atomic nitrogen into the chamber 40, during which a third non-zero concentration of atomic nitrogen is imposed in the chamber 40. The third concentration may be identical to or different from the first concentration. The third concentration may be identical to or different from the second concentration.

In the example of conditioning C shown, the pressure in the chamber 40 begins by increasing from the vacuum pressure Pv to a level value P1 during the stage IA3. The pressure in the chamber 40 is then stabilized at this level value P1 during the stage IA3. This level value may lie in the range 6 mbar to 10 mbar. By way of example, the duration $d_{13}$ of the third injection stage IA3 may be greater than or equal to 5 min, and for example it may lie in the range 5 min to 15 min.

Thereafter, the injection of atomic nitrogen into the chamber 40 is interrupted.

In the example shown, the third injection stage IA3 constitutes the last stage of injecting atomic nitrogen in the conditioning C.

In this example, the conditioning C includes a transition stage PT that is performed after the last stage IA3 of injecting atomic nitrogen and before the beginning of the sterilization step S1. The presence of this transition stage PT is optional.

The transition stage PT comprises a first additional suction stage A5 during which the chamber 40 is evacuated. In this example, the pressure in the chamber 40 decreases progressively from the level value P1 reached during the last injection stage IA3 down to the vacuum pressure Pv. The vacuum pressure Pv reached at the end of this first additional suction stage A5 may be less than or equal to 1 mbar.

Thereafter, during the transition stage PT, an additional stage ID3 of injecting molecular nitrogen into the chamber 40 is performed. In this example, the pressure in the chamber 40 increases from the vacuum pressure Pv to a level value P1 during the stage ID3. Thereafter, the pressure in the chamber 40 is stabilized at this level value P1 during the additional stage ID3 of injecting molecular nitrogen. This level value may lie in the range 6 mbar to 10 mbar. By way of example, the duration $d_{23}$ of the additional injection stage ID3 may be less than or equal to 5 min, and for example may lie in the range 1 min to 5 min.

Thereafter, the injection of molecular nitrogen into the chamber 40 is interrupted.

A second additional suction stage A6 is then performed during which the chamber 40 is evacuated. In this example, the pressure in the chamber 40 decreases progressively from the level value P1 reached during the additional injection stage ID3 down to the vacuum pressure Pv. The vacuum pressure Pv reached at the end of this second additional suction stage A6 may be less than or equal to 1 mbar.

The example of conditioning C shown has three stages IA1-IA3 of injecting atomic nitrogen. Nevertheless, it would not go beyond the ambit of the invention when the conditioning comprises only two stages of injecting atomic nitrogen, or indeed when it comprises more than three stages of injecting atomic nitrogen.

The example of conditioning C shown includes a stage ID1-ID3 of injecting molecular nitrogen that is performed between two suction stages. In the example shown, the durations of these stages ID1-ID3 are less than the durations of the stages IA1-IA3. Between the stages of injecting atomic nitrogen, it is possible to perform a stage of injecting molecular nitrogen and at least one suction stage that may be performed before or after the stage of injecting molecular nitrogen. Nevertheless, it would not go beyond the ambit of the invention if the conditioning did not have such stages of injecting molecular nitrogen.

The method continues by performing a sterilization step S1 using atomic nitrogen. It should be observed that it is possible to obtain partial destruction of the microorganisms present at the end of the conditioning C. In a variant, the conditioning C need not have any sterilizing effect.

The sterilization step S1 performed after the conditioning C serves to obtain a sterile state. The duration of sterilization step S1 may suffice to obtain an at least 6 log reduction in the number of microorganisms present relative to the start of the stage of conditioning C. In other words, under such circumstances, there remain fewer than one microorganism per million at the end of the sterilization step S1, compared with the number of microorganisms that were present at the beginning of the conditioning C. This reduction may be of at least 12 log.

In this example, the sterilization step S1 comprises injecting IA10 atomic nitrogen into the chamber 40. During this injection IA10, a concentration of atomic nitrogen in the chamber 40 is imposed that is greater than any of the atomic nitrogen concentrations that were imposed during the injection stages IA1-IA3.

During the sterilization injection IA10, the pressure in the chamber 40 increases initially from the vacuum pressure Pv to a level value P2. The pressure in the chamber 40 is then stabilized at this level value P2 during the sterilization injection IA10. As shown, the level value P2 is higher than the level value P1 reached during each of the injection stages IA1-IA3 of the conditioning C. The level value P2 may be greater than or equal to 10 mbar. The duration $d_{10}$ of the sterilization injection IA10 may be greater than or equal to 75 min. In the example of FIG. 2, atomic nitrogen is injected IA10 continuously (without interruption) during the sterilization step S1. It would not go beyond the ambit of the invention if the procedure was otherwise, as is described below.

In the example of FIG. 2, the pressure P2 reached during the sterilization injection IA10 is higher than the pressure P1 reached during each of the stages IA1-IA3 of injecting atomic nitrogen. The atomic nitrogen concentration imposed during the sterilization step S1 is thus higher than the concentration imposed during the injection stages IA1-IA3. The pressure may be increased during the sterilization injection IA10 by imposing a flow rate for injecting atomic nitrogen during this injection IA10 that is higher than the atomic nitrogen injection flow rate imposed during each of the injection stages IA1-IA3. This increase in the injection flow rate may be obtained by increasing the flow rate of the air stream 7, and thus of the dinitrogen stream 16. In a variant, or in combination with this increase in flow rate, it is possible to increase the pressure during the injection IA10 by reducing the intensity of suction by the vacuum pump 48.

Nevertheless, it would not go beyond the ambit of the invention if the pressure reached during the sterilization step were not greater than the pressure reached during the stages of injecting atomic nitrogen during the conditioning. Specifically, it is possible to modulate the imposed concentration of atomic nitrogen by modifying the power of the microwave generator 22 used to form the plasma upstream from the chamber 40. It is thus possible to increase the concentration of atomic nitrogen during the sterilization step by increasing that power but without increasing the pressure in the chamber.

By way of illustration, and regardless of the implementation under consideration, at least one of the following conditions may be satisfied:

the first, second, and optional third concentrations may each be less than or equal to $10^{13}$ atoms per cubic centimeter (atom/cm$^3$), e.g. lying in the range $10^{10}$ atom/cm$^3$ to $10^{13}$ atom/cm$^3$; and/or the atomic nitrogen concentration imposed in the chamber during the sterilization step may be greater than or equal to $10^{13}$ atom/cm$^3$, e.g. lying in the range $10^{13}$ atom/cm$^3$ to $10^{16}$ atom/cm$^3$.

Figure 4:
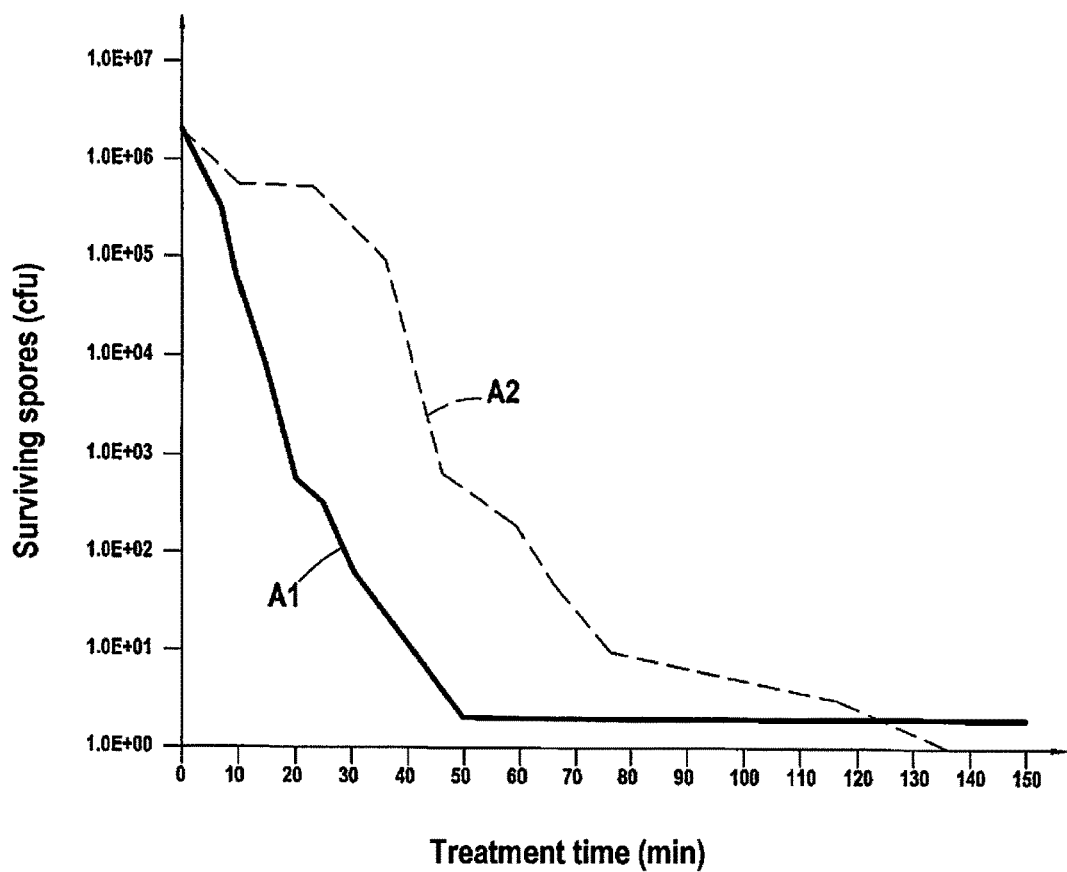
FIG. 4 shows the results obtained in terms of sterilization in the context of the first example of the method of the invention.

FIG. 4 shows an experimental result revealing the improved effectiveness of sterilization associated with performing a method as shown in FIG. 2.

In this graph, the ordinate axis represents colony forming units (cfu), and the abscissa axis represents treatment time. The strain used was a *geobacillus stearothermophillus* strain. Curve A1 relates to performing a sterilization step S1 without conditioning C, while curve A2 relates to performing a sterilization step S1 with preliminary conditioning C.

In the test performed:
the pressure P1 was 8 mbar;
the pressure P2 was 10 mbar;
the pressure Pv was 0.3 mbar;
the durations $d_{11}$, $d_{12}$, and $d_{13}$ were 10 min;
the durations $d_{21}$, $d_{22}$, and $d_{23}$ were 2 min;
the durations of each of the suction stages A1-A6 were 30 seconds (s); and
the temperature imposed during sterilization was less than 60° C.

It can be seen that there exists a saturation phenomenon from about 50 min when the conditioning C is not performed. This saturation means that there continues to remain some quantity of microorganisms that are not destroyed by the sterilization treatment, even if it is prolonged. When conditioning C is performed, curve A2 shows that saturation is no longer encountered and that a sterile state (6 log reduction) can be obtained.

FIG. 3 shows a variant sterilization step S2 performed after the conditioning C. In this variant, the sterilization step S2 comprises a plurality of successive injections IA20 and IA21 of atomic nitrogen. Two consecutive injections IA20 and IA21 of atomic nitrogen are separated by a sequence comprising:
a first suction A20 or A21;
an injection ID20 or ID21 of molecular nitrogen that is performed after the first suction A20 or A21; and
a second suction A20 or A21 performed after injecting ID20 or ID21 molecular nitrogen.

In this example, the pressure reached in the chamber during the injections IA20 and IA21 of concentration is higher than the pressure reached during the stages IA1-IA3 of injecting atomic nitrogen. This thus imposes an atomic nitrogen concentration during the sterilization step S2 that is greater than that imposed during the conditioning C. Each injection IA20 or IA21 of atomic nitrogen in this example includes a period of pressure stabilization to a level value P20 or P21. In this example, each of the level values P20 and P21 is higher than the pressure P1 reached during the stages IA1-IA3 of injecting atomic nitrogen. In the example shown, the level value P21 is also higher than the level value P20.

Figure 5:
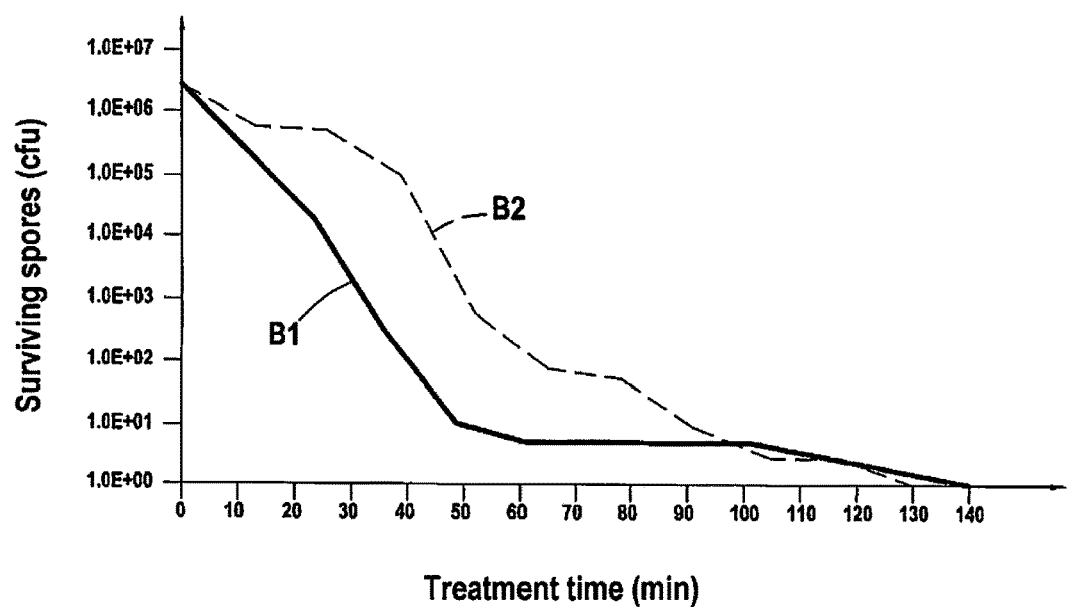
FIG. 5 shows the results obtained in terms of sterilization in the context of the second example of the method of the invention.

FIG. 5 shows an experimental result revealing the improvement in sterilization effectiveness associated with performing a method as shown in FIG. 3.

In this graph, the ordinate axis represents colony forming units (cfu), and the abscissa axis represents treatment time. The strain used was a *geobacillus stearothermophillus* strain. The curve B1 relates to performing a sterilization step S2 without conditioning C, and the curve B2 to performing a sterilization step S2 with preliminary conditioning C.

In the test performed:
the conditioning C was identical to that performed in the context of the test of FIG. 4;
the pressure P20 was 10 mbar;
the pressure P21 was 12 mbar;
the duration of each of the steps IA20 and IA21 was 10 min;
the duration of each of the steps ID20 and ID21 was 2 min;
the durations of each of the suction stages A20 and A21 was 30 s;
the sterilization step S2 was repeated a second time after raising the pressure to atmospheric pressure; and
the temperature imposed during sterilization was less than 60° C.

Curve B1 shows that performing the sterilization step S2, even without conditioning C, already serves to obtain good results.

In addition, for the curve B2, the conditioning C was initially performed for a duration of 39 min followed by the sterilization step S2. Under such conditions, a 6 log reduction in the number of microorganisms was obtained in 130 min. Thus, the duration that serves to obtain a 1 log reduction in the number of microorganisms for the sterilization step S2 in this context is evaluated as (130 min−39 min)/6, i.e. about 15.17 min. The duration of a complete sterilization cycle enabling a 12 log reduction to be obtained in the number of microorganisms under such conditions can then be evaluated as (15.17 min*12)+39 min, i.e. 221 min.

For curve B1, where conditioning was not performed, a 6 log reduction in the number of microorganisms was obtained in 140 min. The duration of a complete sterilization cycle making it possible to obtain a 12 log reduction can then be evaluated as (140 min*2), i.e. 280 min. Performing the conditioning C thus makes it possible to improve significantly the effectiveness of the sterilization step S2 that is performed subsequently.

The term "lying in the range . . . to . . . " should be understood as including the bounds.

The invention claimed is:

1. A method of sterilizing an object with atomic nitrogen from a nitrogen plasma, the method comprising at least:
    positioning the object in a sterilization chamber;
    conditioning the object present in the sterilization chamber, wherein the conditioning includes
        a first stage of injecting atomic nitrogen into the sterilization chamber, during which a first concentration of atomic nitrogen in the sterilization chamber is imposed,
        a suction stage performed after the first injection stage, during which the sterilization chamber is evacuated,
        a stage of injecting molecular nitrogen into the sterilization chamber that is performed after the suction stage, and
        a second stage of injecting atomic nitrogen into the sterilization chamber that is performed after the stage of injecting molecular nitrogen, during which a second concentration of atomic nitrogen is imposed in the sterilization chamber; and wherein the injected atomic nitrogen comes from or is part of a nitrogen plasma generated by a plasma generator from a nitrogen stream, and wherein said nitrogen stream is injected into the sterilization chamber with the plasma generator being switched off during the stage of injecting molecular nitrogen, and
    sterilizing the object, performed after the conditioning, comprising injecting atomic nitrogen into the sterilization chamber, during which step a concentration of atomic nitrogen in the sterilization chamber is imposed that is greater than the first and second concentrations.

2. A method according to claim 1, wherein the conditioning comprises:
    a first suction stage performed after the first stage of injecting atomic nitrogen, during which the sterilization chamber is evacuated;
    the stage of injecting molecular nitrogen into the sterilization chamber that is performed after the first suction stage; and
    a second suction stage performed after the stage of injecting molecular nitrogen, during which the sterilization chamber is evacuated, the second stage of injecting atomic nitrogen into the sterilization chamber being performed after the second suction stage.

3. A method according to claim 2, wherein the duration of the stage of injecting molecular nitrogen is shorter than at least one of the durations of the first and second stages of injecting atomic nitrogen.

4. A method according to claim 3, wherein the duration of the stage of injecting molecular nitrogen is shorter than each of the durations of the first and second stages of injecting atomic nitrogen.

5. A method according to claim 2, wherein the conditioning further comprises:
- a third suction stage performed after the second stage of injecting atomic nitrogen, during which the sterilization chamber is evacuated;
- a second stage of injecting molecular nitrogen into the sterilization chamber, performed after the third suction stage;
- a fourth suction stage performed after the second stage of injecting molecular nitrogen, during which the sterilization chamber is evacuated; and
- a third stage of injecting atomic nitrogen into the sterilization chamber, performed after the fourth suction stage and during which a third atomic nitrogen concentration is imposed in the sterilization chamber;
- the atomic nitrogen concentration in the sterilization chamber that is imposed during the sterilization step being greater than each of the first, second, and third concentrations.

6. A method according to claim 1, wherein the conditioning further comprises, after its last stage of injecting atomic nitrogen, a transition stage comprising at least one additional suction stage, during which the sterilization chamber is evacuated.

7. A method according to claim 6, wherein the transition stage comprises two additional suction stages separated by a stage of injecting molecular nitrogen into the sterilization chamber.

8. A method according to claim 1, wherein the pressure reached in the sterilization chamber during the injection of atomic nitrogen in the sterilization step is higher than the pressure reached in the sterilization chamber during each of the first and second stages of injecting atomic nitrogen.

9. A method according to claim 8, wherein the pressure reached in the sterilization chamber during the injection of atomic nitrogen in the sterilization step is greater than or equal to 10 mbar.

10. A method according to claim 8, wherein the pressure reached in the sterilization chamber during each of the first and second stages of injecting atomic nitrogen lies in the range 6 mbar to 10 mbar.

11. A method according to claim 1, wherein the object is a medical instrument.

12. A method according to claim 5, wherein the pressure reached in the sterilization chamber during the injection of atomic nitrogen in the sterilization step is higher than the pressure reached in the sterilization chamber during each of the first, second, and third stages of injecting atomic nitrogen.

13. A method according to claim 5, wherein the pressure reached in the sterilization chamber during each of the first, second, and third stages of injecting atomic nitrogen lies in the range 6 mbar to 10 mbar.

* * * * *